(12) United States Patent
Busch

(10) Patent No.: US 10,426,161 B2
(45) Date of Patent: Oct. 1, 2019

(54) SOLID ANTIMICROBIAL COMPOSITIONS WITH ENHANCED SOLUBILITY

(71) Applicant: Biosyn LLC, Clementon, NJ (US)

(72) Inventor: Frederick A. Busch, Clementon, NJ (US)

(73) Assignee: Biosyn Inc, Littleton, CO (US)

( * ) Notice: Subject to any disclaimer, the term of this patent is extended or adjusted under 35 U.S.C. 154(b) by 121 days.

(21) Appl. No.: 14/993,588

(22) Filed: Jan. 12, 2016

(65) Prior Publication Data

US 2016/0227775 A1    Aug. 11, 2016

Related U.S. Application Data

(60) Provisional application No. 62/125,086, filed on Jan. 13, 2015.

(51) Int. Cl.
*A01N 43/40* (2006.01)
*A01N 33/12* (2006.01)

(52) U.S. Cl.
CPC .................................. *A01N 33/12* (2013.01)

(58) Field of Classification Search
CPC .............................. A01N 43/40; A01N 33/12
USPC ......................................................... 424/408
See application file for complete search history.

(56) References Cited

U.S. PATENT DOCUMENTS

| | | | |
|---|---|---|---|
| 5,112,520 A * | 5/1992 | Krinski | C11D 3/382 106/154.3 |
| 8,075,936 B2 | 12/2011 | Burwell et al. | |
| 8,080,269 B2 | 12/2011 | Burwell et al. | |
| 8,586,115 B2 | 11/2013 | Burwell et al. | |
| 8,853,278 B1 | 10/2014 | Looper et al. | |
| 8,962,662 B2 | 2/2015 | Busch et al. | |
| 9,095,731 B2 | 8/2015 | Gentle et al. | |
| 9,265,248 B2 | 2/2016 | Gentle et al. | |
| 2003/0104969 A1 * | 6/2003 | Caswell | A47F 1/08 510/513 |
| 2005/0238631 A1 | 10/2005 | Burwell | |
| 2009/0312215 A1 * | 12/2009 | Glenn | A47L 13/10 510/158 |
| 2010/0003212 A1 | 1/2010 | Kis et al. | |
| 2010/0190004 A1 * | 7/2010 | Gibbins | A61F 13/02 428/346 |
| 2011/0301070 A1 * | 12/2011 | Ochomogo | C11D 3/0052 510/180 |
| 2012/0048769 A1 * | 3/2012 | Sivik | B29C 43/006 206/524.1 |
| 2012/0171301 A1 | 7/2012 | Koenig et al. | |
| 2012/0196953 A1 | 8/2012 | Ziolkowski et al. | |
| 2012/0297551 A1 * | 11/2012 | Grande | C11D 3/398/137 |
| 2012/0329881 A1 * | 12/2012 | Crossley | A01N 31/02 514/724 |
| 2014/0294749 A1 | 10/2014 | Gentle et al. | |

FOREIGN PATENT DOCUMENTS

| | | |
|---|---|---|
| EP | 1863865 B1 | 5/2012 |
| WO | 2008/008362 A2 | 1/2008 |

OTHER PUBLICATIONS interspersed. (n.d.). Dictionary.com Unabridged. Retrieved Mar. 24, 2018 from Dictionary.com website http://www.dictionary.com/browse/interspersed.*
PCT International Search Report and Written Opinion for PCT Application No. PCT/US2016/013017 dated Apr. 21, 2016 (14 pages).

* cited by examiner

*Primary Examiner* — Johann R Richter
*Assistant Examiner* — Courtney A Brown
(74) *Attorney, Agent, or Firm* — Eversheds Sutherland (US) LLP

(57) ABSTRACT

The present disclosure generally provides for antimicrobial compositions having enhanced solubility and methods of using the same. The antimicrobial compositions are suitable for reducing or preventing microorganism growth, viability, or survival. The antimicrobial compositions generally include at least one antimicrobial quaternary ammonium compound and a water-soluble spacer compound or spacer interspersed therewith.

19 Claims, No Drawings

SOLID ANTIMICROBIAL COMPOSITIONS WITH ENHANCED SOLUBILITY

CROSS REFERENCE TO RELATED APPLICATIONS

This application claims priority benefit of U.S. Provisional Application No. 62/125,086, filed Jan. 13, 2015, which is incorporated by reference herein in its entirety.

FIELD OF THE DISCLOSURE

The present disclosure generally relates to antimicrobial compositions and methods for reducing or preventing microorganism growth, viability, or survival.

BACKGROUND OF THE DISCLOSURE

Antimicrobials are chemical compounds which reduce or mitigate the growth or development of microorganisms such as pathogenic bacteria, fungi and viruses. The use of antimicrobial compounds leads to either death or arrested growth of the targeted microorganisms. Antimicrobial agents have transformed the prevention and treatment of infectious diseases and are employed across a very broad spectrum of applications.

Of the diverse categories of antimicrobial agents and compositions, quaternary ammonium compounds represent one of the largest classes of agents in use. Quaternary ammonium compounds serve as the active antimicrobial agent in a wide variety of formulations which are currently used in the household, industrial and institutional markets. For example, quaternary ammonium compounds are used in restaurants, dairies, food storage and processing operations, laundries and medical facilities. Quaternary ammonium compounds are typically effective over a broad range of concentrations and are bactericidal, fungicidal, algicidal, sporicidal, and viricidal.

Quaternary ammonium salts usually exhibit relatively slow and/or low solubility in water and foam when dissolved and stirred. As a result, quaternary ammonium based antimicrobials are shipped as concentrated liquids for both ease of formulation and rapid solubility. At present, millions of pounds of concentrated antimicrobial solutions containing a quaternary ammonium compound dissolved in a solvent are shipped both domestically and globally. When shipments are received, the antimicrobial solution is diluted to achieve the appropriate formulation.

Concentrated antimicrobial solutions in plastic containers can weigh as much as 8 to 9 pounds per gallon and consume significant space in shipping containers. The considerable weight and size of both the antimicrobial solutions and the plastic containers containing them increases the transportation costs associated with shipping (e.g. fuel expenses, shipping labor). In addition, concentrated antimicrobial solutions are liable to freeze in colder climates during shipping. Beyond transportation concerns, commercial, industrial and consumer use of antimicrobial solutions generate storage and waste management issues. For example, antimicrobial solutions for consumer use are packaged in plastic bottles, which occupy warehouse, store, and home space, as well as contribute to disposable waste.

The fiscal, environmental, and other costs associated with distribution and use of quaternary ammonium based antimicrobials are substantial. Accordingly, there remains a need for improved quaternary ammonium based antimicrobial compositions that can address the shortcomings of the current quaternary ammonium based antimicrobial compositions.

SUMMARY OF THE INVENTION

This disclosure generally provides compositions and methods for reducing or preventing microorganism growth, viability, or survival. In some aspects, an antimicrobial composition is provided that comprises at least one antimicrobial quaternary ammonium compound and a water-soluble spacer compound interspersed therewith. In some aspects or embodiments, the antimicrobial composition can further comprise one or more oxidizers, non-ionic surfactants, additional antimicrobial compounds, chelators, detergents, and combinations thereof. In other aspects, the antimicrobial composition can be packaged in a unit dose form. In some aspects or embodiments, the antimicrobial composition can be encapsulated in water-soluble packaging. In other embodiments, the antimicrobial quaternary ammonium compound and the water-soluble spacer compound are encapsulated separately from an oxidizer. According to further aspects or embodiments provide the antimicrobial composition as a powder, a gel, or a slurry. Some aspects provide that the at least one antimicrobial quaternary ammonium compound can be about 50% to about 95% by weight of the antimicrobial composition and the water-soluble spacer compound can be about 5% to about 50% by weight of the antimicrobial composition.

In some aspects or embodiments, a method of making an antimicrobial composition is provided that comprises admixing at least one antimicrobial quaternary ammonium compound with a water-soluble spacer compound. In some embodiments, the method further comprises including one or more oxidizers, non-ionic surfactants, additional antimicrobial compounds, chelators, detergents, and combinations thereof, in the antimicrobial composition. In some embodiments, the method comprises encapsulating the antimicrobial composition in water-soluble packaging. In some embodiments, the method comprises encapsulating the antimicrobial quaternary ammonium compound and the water-soluble spacer compound separately from an oxidizer. In some embodiments, the method comprises providing an antimicrobial composition as a powder, gel, or a slurry. In some embodiments, the method comprises providing an antimicrobial composition wherein the at least one antimicrobial quaternary ammonium compound can be about 50% to about 95% by weight of the antimicrobial composition and the water-soluble spacer compound can be about 5% to about 50% by weight of the antimicrobial composition.

In some embodiments, a method for sanitizing using an antimicrobial composition is provided that includes dissolving or diluting an antimicrobial composition comprising at least one antimicrobial quaternary ammonium compound and a water-soluble spacer compound interspersed therewith in a solvent to form a cleaning solution, and contacting an area or an item with the cleaning solution.

DETAILED DESCRIPTION OF THE INVENTION

Aspects will be set forth in part in the description that follows, and in part will be obvious from the description, or may be learned by practice of the aspects described below. The advantages described below will be realized and attained by means of the elements and combinations particularly pointed out in the appended claims. It is to be understood that the following detailed description is exemplary and explanatory only and is not restrictive.

In the following description, numerous specific details are given to provide a thorough understanding of embodiments. The embodiments can be practiced without one or more of the specific details, or with other methods, components, materials, and the like. In other instances, well-known structures, materials, or operations are not shown or described in detail to avoid obscuring aspects of the embodiments. It is to be understood that the aspects described below are not limited to specific synthetic methods or specific reagents, and as such may vary. It is also to be understood that the terminology used herein is for the purpose of describing particular aspects only and is not intended to be limiting.

Any headings that may be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls. Thus, in this specification and in the claims that follow, reference will be made to a number of terms, which shall be defined to have the following meanings:

As used in the specification and the appended claims, the singular words "a," "an," and "the" include the plural unless the context clearly dictates otherwise. Thus, for example, reference to "a compound" includes mixtures or combinations of two or more such compounds, reference to "an agent" includes mixtures of two or more such agents, reference to "the composition" includes mixtures of two or more such compositions, and the like.

Throughout the specification and claims, the word "comprise" and variations of the word such as "comprising" and "comprises," mean "including but not limited to," and are not intended to exclude, for example, other additives, components, integers, or steps.

"Optional" or "optionally" means that the subsequently described event or circumstance can or cannot occur, and that the description includes instances where the event or circumstance occurs and instances where it does not.

Reference throughout this specification to "one embodiment," "an embodiment," or "embodiments" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed herein, and that each value is also herein disclosed as "about" that particular value in addition to the value itself. In aspects, "about" can be used to mean within ±10% of the recited value. In other aspects, "about" can be used to mean within ±5% of the recited value, ±2% of the recited value, or ±1% of the recited value.

Unless indicated otherwise, when a range of any type is disclosed or claimed, for example a range of weight percentages and the like, it is intended that the stated range disclose or claim individually each possible number that such a range could reasonably encompass, including any sub-ranges and combinations of sub-ranges encompassed therein. For example, when describing a range of measurements such as weight percentages, every possible number that such a range could reasonably encompass can, for example, refer to values within the range with more significant digits than are present in the end points of a range. For example, a weight percentage between 10 percent and 20 percent includes individually 10, 11, 12, 13, 14, 15, 16, 17, 18, 19, and 20 weight percent. Applicant reserves the right to proviso out or exclude any individual members of any such group, including any sub-ranges or combinations of sub-ranges within the group, if for any reason Applicant chooses to claim less than the full measure of the disclosure.

A weight percent of a component, unless specifically stated to the contrary, is based on the total weight of the formulation or composition in which the component is included, according to its usual definition.

The term "reduce" and other forms of the word such as "reducing" or "reduction" mean lowering of an event or characteristic (e.g., microorganism growth, viability, or survival). Lowering of an event or characteristic is typically in relation to some standard or expected value (i.e. reduction is a relative term). However, it is not always necessary for the standard or relative value to be referred to. For example, "reduces the population of bacteria" means lowering the amount of bacteria relative to a standard or a control.

The term "prevent" and other forms of the word such as "preventing" or "prevention" mean stopping a particular event or characteristic, stabilizing or delaying the development or progression of a particular event or characteristic, or minimizing the chances that a particular event or characteristic will occur. Prevent does not require comparison to a reference as it is typically more absolute than, for example, the term reduce. As used herein, something could be reduced but not prevented, but something that is reduced could also be prevented. Likewise, something could be prevented but not reduced, but something that is prevented could also be reduced.

The term "treat" and other forms of the word such as "treated" or "treatment" mean administering a composition or performing a method in order to reduce, prevent, inhibit, break-down, or eliminate a particular characteristic or event (e.g., microorganism growth, viability, or survival). It is generally understood that treating involves contacting an area or an item with a solution derived from the antimicrobial compositions disclosed herein.

The term "substantially free", for example when describing a composition that is substantially free of a particular component, such as a compound or material, is meant to reflect that none of the recited component is intentionally added or used in the subject composition.

The term "antimicrobial" means the ability to treat (e.g., reduce, prevent, inhibit, break-down, or eliminate) microorganism growth, viability, or survival at any concentration.

Reference will now be made in detail to specific aspects of the disclosed materials, compounds, compositions, components, devices, articles, and methods, examples of which are illustrated in the following description and examples, and in their previous and following description.

The disclosure provides, among other things, compositions and methods for reducing or preventing microorganism growth, viability, or survival.

According to one aspect of this disclosure, there is provided an antimicrobial composition that comprises at least one antimicrobial quaternary ammonium compound and a water-soluble spacer compound interspersed therewith. Exemplary antimicrobial quaternary ammonium compounds include benzyltrimethylammonium chloride (BTAC), benzethonium chloride (BEC), cetylpyridinium chloride (CPC), cetyltrimethylammonium chloride (CTAC), alkyldimethylbenzylammonium chloride (C8 to C18 in all varieties) (ADBAC), alkyldimethylethylbenzylammonium chloride (ADEBAC), didecyldimethylammonium chloride (DDC), dialkydimethylammonium chloride (DDAC), cocamidopropyl PG-dimonium chloride phosphate (Cola Lipid C), and combinations thereof. Exemplary water-soluble spacer compounds include but are not limited to sodium bicarbonate, sodium chloride, urea, sugar, carrageenan, hydroxyethyl cellulose, methylcellulose, hydroxycellulose, and polyethylene oxide. Properties of suitable spacer compounds include their existence in the solid state at typical compounding and storage temperatures, their water-solubility, and their compatibility and lack of reactivity (or extremely slow reactivity) with the quaternary ammonium compound at typical compounding and storage conditions, such as temperature. Generally, the spacer compound is a compound different from the antimicrobial quaternary ammonium compounds, non-ionic surfactants, additional antimicrobial compounds, chelators, and detergents disclosed herein. Spacer compounds can be complex mixtures or combinations of compounds and are not limited to a single molecular species, for example, carrageenan is referred to herein as a spacer compound even though it generally constitutes a family of linear sulfated polysaccharide compounds. Based on this disclosure, other suitable antimicrobial quaternary ammonium compounds and water-soluble spacer compounds will be appreciated by those skilled in the art.

In some embodiments, the at least one antimicrobial quaternary ammonium compound comprises about 50% to about 95% by weight of the antimicrobial composition and the water-soluble spacer compound comprises about 5% to about 50% by weight of the antimicrobial composition. In some embodiments, the at least one antimicrobial quaternary ammonium compound and the water-soluble nucleation are present in the antimicrobial composition at a weight ratio of about 85:15 relative to one another, regardless of whether additional components are contained in the antimicrobial composition.

Further aspects or embodiments provide that the at least one antimicrobial quaternary ammonium compound can comprise, by weight, about 45%, about 50%, about 55%, about 60%, about 65%, about 70%, about 75%, about 80%, about 85%, about 90%, about 95%, or about 97% of the combined antimicrobial quaternary ammonium compound and the water-soluble spacer compound not including any additional components. Accordingly, these aspects or embodiments provide that the water-soluble spacer compound can comprise, by weight, about 3%, about 5%, about 10%, about 15%, about 20%, about 25%, about 30%, about 35%, about 40%, about 45%, about 50%, or about 55%, of the combined antimicrobial quaternary ammonium compound and the water-soluble spacer compound not including any additional components.

In some embodiments, the antimicrobial composition further comprises one or more oxidizers, non-ionic surfactants, additional antimicrobial compounds, chelators, detergents, and combinations thereof. When these additional components are present, the combined additional components can constitute about 0.01%, about 0.02%, about 0.05%, about 0.1%, about 0.2%, about 0.5%, about 1%, about 2%, about 5%, about 7%, about 10%, about 15%, about 20%, about 25%, about 30%, about 35%, about 40%, about 45%, about 50%, about 55%, 60%, about 65%, about 70%, or about 75% by weight of the antimicrobial composition. Accordingly, these aspects or embodiments provide that the combined antimicrobial quaternary ammonium compound and the water-soluble spacer compound can comprise, by weight, about 99.99%, about 99.98%, about 99.95%, about 99.9%, about 99.8%, about 99.5%, about 99%, about 98%, about 95%, about 93%, about 90%, about 85%, about 80%, about 75%, about 70%, about 65%, about 60%, about 55%, about 50%, about 45%, about 40%, about 35%, about 30%, or about 25% of the antimicrobial composition.

Exemplary oxidizers include trichloromelamine (TCM), dichloroisocyanurate (DCI), trichloroisocyanurate (TCI), and potassium perborate. Exemplary non-ionic surfactants include an ethoxylated aliphatic alcohol, a polyoxyethylene surfactant, a carboxylic ester, a polyoxyethylene glycol ester, an anhydrosorbital ester, an ethoxylated derivative of an anhydrosorbital ester, a glycol ester of a fatty acids, a carboxylic amide, a monoalkanolamine condensate, and a polyoxyethylene fatty acid amide. Exemplary detergents include TRITON™ X-100 (4-(1,1,3,3-Tetramethylbutyl) phenyl-polyethylene glycol) (CAS Registry Number: 9002-93-1) (linear formula: $C_{14}H_{22}O(C_2H_4O)_n$ where n=9-10), TERGITOL™ 15-S (general structural formula: $C_{12-14}H_{25-29}O[CH_2CH_2O]_nH$), and sodium laurel sulfate. Exemplary additional antimicrobial compounds include monolaurin, methylisothiazolinone, chloromethylisothiazolinone, nisin, and ε-polylysine. Exemplary chelators include ethylenediaminetetraacetic acid (EDTA). Other suitable oxidizers, non-ionic surfactants, additional antimicrobial compounds, chelators, and detergents are obvious to those skilled in the art.

In addition to the components disclosed above, the disclosed antimicrobial compositions can be in the form of an aqueous solution, thus, water or another solvent can be another component of the disclosed compositions.

In some embodiments, the one or more antimicrobial quaternary ammonium compounds collectively total about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, 600, 600, 610, 620, 630, 640, 650, 660, 670, 680, 690, 700, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 parts per million (ppm) of active antimicrobial quaternary ammonium compounds when the antimicrobial composition is reconstituted or diluted for final use (e.g. for use by the end-user). In some preferred embodiments, the one or more antimicrobial quaternary ammonium compounds collectively total no more than 500 ppm of active antimicrobial quaternary ammonium compounds when the antimicrobial compositions are reconstituted or diluted for final use (e.g. for use by the end-user).

In embodiments comprising one or more oxidizers such as TCM, DCI, and TCI, the oxidizers collectively total about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, 600, 600, 610, 620, 630, 640, 650, 660, 670, 680, 690, 700, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, or 2000 ppm of active chlorine when the antimicrobial compositions are reconstituted or diluted for final use (e.g. for use by the end-user). In embodiments comprising one or more oxidizers such as TCM, DCI, and TCI, it is sometimes preferable that the oxidizers collectively total no more than 200 ppm of active chlorine when the antimicrobial compositions are reconstituted or diluted for final use (e.g. for use by the end-user).

In some embodiments, one or more components in the antimicrobial composition (e.g. antimicrobial quaternary ammonium compounds, water-soluble spacer compounds, oxidizers, non-ionic surfactants, additional antimicrobial compounds, chelators, and detergents) can be individually present in an amount from less than about 95 weight %, less than about 85 weight %, less than about 75 weight %, less than about 65 weight %, less than about 55 weight %, less than about 50 weight %, less than about 45 weight %, less than about 40 weight %, less than about 35 weight %, less than about 30 weight %, less than about 25 weight %, less than about 20 weight %, less than about 15 weight %, less than about 10 weight %, less than about 8 weight %, less than about 6 weight %, less than about 5 weight %, less than about 4 weight %, less than about 3 weight %, less than about 2 weight %, less than about 1 weight %, less than about 0.5 weight %, less than about 0.1 weight %, less than about 0.05 weight %, less than about 0.01 weight %, less than about 0.005 weight %, or less than about 0.001 weight % based on the total weight of the antimicrobial composition. In some embodiments, one or more components in the antimicrobial composition (e.g. antimicrobial quaternary ammonium compounds, water-soluble spacer compounds, oxidizers, non-ionic surfactants, additional antimicrobial compounds, chelators, and detergents) can be individually present in an amount from greater than about 0.001 weight %, greater than about 0.005 weight %, greater than about 0.01 weight %, greater than about 0.05 weight %, greater than about 0.1 weight %, greater than about 0.5 weight %, greater than about 1 weight %, greater than about 2 weight %, greater than about 3 weight %, greater than about 4 weight %, greater than about 5 weight %, greater than about 6 weight %, greater than about 8 weight %, greater than about 10 weight %, greater than about 15 weight %, greater than about 20 weight %, greater than about 25 weight %, greater than about 30 weight %, greater than about 35 weight %, greater than about 40 weight %, greater than about 45 weight %, greater than about 50 weight %, greater than about 60 weight %, greater than about 70 weight %, greater than about 80 weight %, or greater than about 90 weight %, based on the total weight of the antimicrobial composition. In some embodiments, one or more components in the antimicrobial composition (e.g. antimicrobial quaternary ammonium compounds, water-soluble spacer compounds, oxidizers, non-ionic surfactants, additional antimicrobial compounds, chelators, and detergents) can be individually present in an amount of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.5, 16.75, 17.0, 17.25, 17.5, 17.75, 18.0, 18.25, 18.5, 18.75, 19.0, 19.25, 19.5, 19.75, 20.0, 21.25, 21.5, 21.75, 22.0, 22.25, 22.5, 22.75, 23.0, 23.25, 23.5, 23.75, 24.0, 24.25, 24.5, 24.75, 25.0 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 weight %, based on the total weight of the antimicrobial composition and where any of the stated values can form an upper or lower endpoint when appropriate. Thus, this disclosure includes any range or combinations of ranges or sub-ranges between and including these values when appropriate.

In some embodiments, one or more components in the antimicrobial composition (e.g. antimicrobial quaternary ammonium compounds, water-soluble spacer compounds, oxidizers, non-ionic surfactants, additional antimicrobial compounds, chelators, and detergents) can be individually present in an amount of about 1, 2, 5, 10, 15, 20, 50, 100, 150, 200, 250, 300, 350, 400, 450, 500, 550, 600, 650, 700, 750, 800, 850, 900, 950, 1000, 1250, 1500, 1750, 2000, 2500, 3000, 3500, 4000, 4500, 5000, 5500, 6000, 6500, 7000, 7500, 8000, 8500, 9000, 10000, 20000, 30000, 40000, 50000, 60000, 70000, 80000, 90000, or 100000 ppm, in the concentrated antimicrobial composition (e.g. a solid state antimicrobial composition or highly concentrated gel or slurry), where any of the stated values can form an upper or lower endpoint when appropriate.

In some embodiments, the antimicrobial compositions are encapsulated in water-soluble packaging. The water-soluble packaging may be made from, for example, polyvinyl alcohol or polyethylene oxide. The type and grade of water-soluble packaging depends on the contents of the antimicrobial composition. For example, only certain grades of polyvinyl alcohol based packaging will be suitable for use with oxidizers such as TCM, DCI, and TCI. The encapsulation in water-soluble packaging can be done according to any routine method known in the industry. For example, an antimicrobial composition can be encapsulated in water-soluble packaging using an automatic filler and a subsequent heat sealing platen. In some embodiments, use of water-soluble packaging further enhances the solubility of the antimicrobial compositions because the water-soluble packaging (e.g. polyvinyl alcohol or polyethylene oxide) can exhibit surfactant properties and further lower the antimicrobial compositions' resistance to dissolution.

In some embodiments, the components of the antimicrobial compositions may be encapsulated together or separately. For example, a unit dose form of an antimicrobial composition in water-soluble packaging may have two or more separate pouches that separately encapsulate different components of the antimicrobial composition. For example, in one embodiment where a water-soluble packaging encapsulates an antimicrobial composition comprising at least one antimicrobial quaternary ammonium compound, a water-soluble spacer compound, and an oxidizer, the at least one antimicrobial quaternary ammonium compound and the water-soluble spacer compound are encapsulated in a first pouch that is separate from a second pouch used to encapsulate the oxidizer.

In some embodiments, one or more components of the antimicrobial compositions can include a binder constituent, particularly when the component is formed into a solid or semi-solid mass such as a cake, tablet, block, briquette, densified powder, prill, or other configuration. For example, an oxidizer may be combined with polyethylene oxide and prilled in order to reduce the reactivity of the of the oxidizer. In a further example, an oxidizer such as trichloromelamine can be prilled, which can protect it from reactivity prior to being dissolved in solution. In some embodiments where an antimicrobial composition comprises at least one antimicrobial quaternary ammonium compound, a water-soluble spacer compound, and an oxidizer, the oxidizer is prilled prior to encapsulation.

In some embodiments, two or more components of the antimicrobial compositions are mixed together before being packaged. For example, an antimicrobial quaternary ammonium compound and a water-soluble spacer compound may be admixed thoroughly using any suitable blender, such as a ribbon blender, before being packaged. Where multiple components of the antimicrobial compositions are mixed together, the components can be admixed in any order.

In some embodiments, the antimicrobial compositions are provided as a dried powder (e.g. a solid), a gel, a slurry, a concentrated liquid, or the antimicrobial compositions can even be supplied as combinations of these forms. In some embodiments, the antimicrobial compositions in unit dose form can be in the form of solid, semi-solid, liquid, or gel forms, such as, for example, tablets, pills, capsules, powders, liquids, suspensions, dispersions, or emulsions. In some embodiments, dried powders are preferable because they have the lowest weight and occupy the least space. However, in some embodiments, it may be preferable to provide the antimicrobial compositions as a highly concentrated gel or slurry, such as when a liquid additive is used. When provided as a gel or slurry, the antimicrobial compositions are typically provided at concentrations of 90% or higher, and typically at about 96%. The antimicrobial compositions can be in a form suitable for dilution. That is, the compositions can be in the form of an aqueous or non-aqueous stock solution, concentrate, concentrated solution, dispersion, emulsion, or suspension that can be diluted to a desired concentration with a suitable solvent (e.g., water). Similarly, the compositions can be in the form of a powder, paste, cream, or solid that can be reconstituted or mixed with a solvent and diluted to a desired concentration to form a solution or dispersion, emulsion, emulsifiable concentrate, slurry, or suspension.

The antimicrobial compositions, whether formulated as a dried powder, a gel, a slurry, a liquid, or a combination thereof, can be encapsulated in water-soluble packaging, packaged in a so-called Menasha box which includes a water-proof liner, or otherwise be packaged by other suitable means known in the art. The appropriate packaging will depend on the components of the antimicrobial composition and the types of packaging appropriate for a particular formulation will be obvious to those skilled in the art.

In some embodiments, the antimicrobial compositions are provided in unit doses. A unit dose means an amount of an antimicrobial composition that, when reconstituted or diluted, is sufficient to provide the desired result (e.g. reduction or prevention of microorganism growth, viability, or survival). As disclosed herein, the exact amount required will vary from use to use depending on a variety of parameters, as understood by one of ordinary skill, such as the type of application, the type of microorganism to be treated, the particular compositions being used, and the like. The determination of what is an appropriate unit dose for a particular formulation can be made by routine testing with known concentrations and adjusting those concentrations as needed to obtain the desired result. Thus, an appropriate unit dose for a particular formulation and application can be determined by one of ordinary skill in the art using only routine experimentation. In some embodiments, the unit doses comprise an antimicrobial composition in sufficient quantity such that, when reconstituted or diluted, the antimicrobial composition produces from about 0.1 gallons to about 10,000 gallons or more of an effective antimicrobial solution.

As disclosed herein, the antimicrobial compositions can be used to treat various surfaces, areas, or items to reduce, inhibit, prevent, disrupt, degrade, breakdown, eliminate, and the like, microorganism growth, viability, or survival. The antimicrobial compositions can also be used to treat microorganisms in aqueous environments.

This disclosure also provides for a method comprising contacting a surface, an area, an item, or the like with an effective amount of an antimicrobial composition. The term "effective amount" of a composition means an amount of an antimicrobial composition that, when reconstituted or diluted, is sufficient to provide the desired result (e.g. reduction or prevention of microorganism growth, viability, or survival). As disclosed herein, the exact amount required will vary from use to use depending on a variety of parameters, as understood by one of ordinary skill, such as the type of application, the type of microorganism to be treated, the particular compositions being used, and the like. The determination of what constitutes an "effective amount" for a particular formulation can be made by routine testing with known concentrations and adjusting those concentrations as needed to obtain the desired result. Thus, an "effective amount" for a particular formulation and application can be determined by one of ordinary skill in the art using only routine experimentation.

The disclosed antimicrobial compositions are effective when concentrated or when diluted with water up to a certain point. For example, the disclosed antimicrobial compositions can be diluted with water in the range of about 1 to about 1000 parts water to one part antimicrobial composition and still perform effectively. In some specific examples, the antimicrobial compositions disclosed herein can be diluted with water in a ratio of about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 101:1, 102:1, 103:1, 104:1, 105:1, 106:1, 107:1, 108:1, 109:1, 110:1, 111:1, 112:1, 113:1, 114:1, 115:1, 116:1, 117:1, 118:1, 119:1, 120:1, 121:1, 122:1, 123:1, 124:1, 125:1, 126:1, 127:1, 128:1, 129:1, 130:1, 131:1, 132:1, 133:1, 134:1, 135:1, 136:1, 137:1, 138:1, 139:1, 140:1, 141:1, 142:1, 143:1, 144:1, 145:1, 146:1, 147:1, 148:1, 149:1, 150:1, 151:1, 152:1, 153:1, 154:1, 155:1, 156:1, 157:1, 158:1, 159:1, 160:1, 161:1, 162:1, 163:1, 164:1, 165:1, 166:1, 167:1, 168:1, 169:1, 170:1, 171:1, 172:1, 173:1, 174:1, 175:1, 176:1, 177:1, 178:1, 179:1, 180:1, 181:1, 182:1, 183:1, 184:1, 185:1, 186:1, 187:1, 188:1, 189:1, 190:1, 191:1, 192:1, 193:1, 194:1, 195:1, 196:1, 197:1, 198:1, 199:1, 200:1, 201:1, 202:1, 203:1, 204:1, 205:1, 206:1, 207:1, 208:1, 209:1, 210:1, 211:1, 212:1, 213:1, 214:1, 215:1, 216:1, 217:1, 218:1, 219:1, 220:1, 221:1, 222:1, 223:1, 224:1, 225:1, 226:1, 227:1, 228:1, 229:1, 230:1, 231:1, 232:1, 233:1, 234:1, 235:1, 236:1, 237:1, 238:1, 239:1, 240:1, 241:1, 242:1, 243:1, 244:1, 245:1, 246:1, 247:1, 248:1, 249:1, 250:1, 251:1, 252:1, 253:1, 254:1, 255:1, 256:1, 257:1, 258:1, 259:1, 260:1, 261:1, 262:1, 263:1, 264:1, 265:1, 266:1, 267:1, 268:1, 269:1, 270:1, 271:1, 272:1, 273:1, 274:1, 275:1, 276:1, 277:1, 278:1, 279:1, 280:1, 281:1, 282:1, 283:1, 284:1, 285:1, 286:1, 287:1, 288:1, 289:1, 290:1, 291:1, 292:1, 293:1, 294:1, 295:1, 296:1, 297:1, 298:1, 299:1, 300:1, 301:1, 302:1, 303:1, 304:1, 305:1, 306:1, 307:1, 308:1, 309:1, 310:1, 311:1, 312:1, 313:1, 314:1, 315:1, 316:1, 317:1, 318:1, 319:1, 320:1, 321:1, 322:1, 323:1, 324:1, 325:1, 326:1, 327:1, 328:1, 329:1, 330:1, 331:1, 332:1, 333:1, 334:1, 335:1, 336:1, 337:1, 338:1, 339:1, 340:1, 341:1, 342:1, 343:1, 344:1, 345:1, 346:1, 347:1, 348:1, 349:1, 350:1, 351:1, 352:1, 353:1, 354:1, 355:1, 356:1, 357:1, 358:1, 359:1, 360:1, 361:1, 362:1, 363:1, 364:1, 365:1, 366:1, 367:1, 368:1, 369:1, 370:1, 371:1, 372:1, 373:1, 374:1, 375:1, 376:1, 377:1, 378:1, 379:1, 380:1, 381:1, 382:1, 383:1, 384:1, 385:1, 386:1, 387:1, 388:1, 389:1, 390:1, 391:1, 392:1, 393:1, 394:1, 395:1, 396:1, 397:1, 398:1, 399:1, 400:1, 450:1, 500:1, 550:1, 600:1, 650:1, 700:1, 750:1, 800:1, 850:1, 900:1, 950:1, or 1000:1, parts water to parts antimicrobial composition; these ratios can also be an upper and lower endpoint of a range of ratios when appropriate.

The advantages of the presently disclosed antimicrobial compositions having enhanced solubility and other aspects of this disclosure are demonstrated in the following Illustrative Embodiments.

Illustrative Embodiments

Conventionally, quaternary ammonium based antimicrobials have been shipped as concentrated liquids for both ease of formulation and rapid solubility because quaternary ammonium salts are usually difficult to solubilize in water. More particularly, quaternary ammonium salts solubilize relatively slow and/or have low solubility in water (they require substantial effort to solubilize), and they foam when dissolved and stirred (stirring generates shear forces that help dissolve the quaternary ammonium salts but also generate foam/bubbles). Without being bound by theory, it is thought that the slow solubility of quaternary ammonium salts may possibly be attributable to a nucleation effect. When added into a solvent such as water, quaternary ammonium compounds tend to adhere in the form of large crystalline clusters or structures and become difficult to solubilize. These large crystal structures slow or effectively prevent solubilization of the inner crystalline structure by the surrounding solvent (e.g. water).

Regardless of the mechanism that makes solubilizing quaternary ammonium salts difficult, it has been unexpectedly discovered that by introducing a highly water-soluble compound that physically separates quaternary ammonium granules or particles from one another (e.g. a physical spacer), a reduction in the slow and/or low solubility can be achieved. Again, without being bound by theory, it appears that any nucleation effects in the quaternary ammonium compound are reduced or minimized by the physical spacer (e.g. the physical spacer appears to function as a nucleation inhibitor and inhibit crystal or clustering in the quaternary ammonium compound). Regardless, the solubility and/or the rate of solubility of the quaternary ammonium molecules is greatly enhanced with the introduction of a highly water-soluble physical spacer, which allows for direct solubilization of powdered, gelled, or slurried quaternary ammonium based antimicrobial compositions. Therefore, the disclosed compositions and methods are improvements over the the current industry custom of transporting quaternary ammonium based antimicrobial compositions as concentrated solutions. For instance, when the disclosed quaternary ammonium based antimicrobial compositions comprise as little as 5% by weight of a water-soluble spacer compound, the antimicrobial compositions readily dissolve when mixed with water. This results in as little as 25 ppm of additive.

The present disclosure can reduce the transportation, environmental, and other fiscal costs associated with the distribution, storage, and use of quaternary ammonium based antimicrobials. For example, the antimicrobial compositions having enhanced solubility can be shipped at weights of less than a kilogram per gallon (e.g. 1 kg/gallon, 1 g/gallon, and the like) whereas ready-to-go antimicrobial solutions weigh a minimum of 8 to 9 pounds per gallon (a gallon of water is 3.785 kg). Further, the antimicrobial compositions having enhanced solubility can be shipped in light-weight, more compact packaging when compared to ready-to-go solutions stored in plastic drums, pails, totes, bottles, and the like. This results in both fuel and space savings during transportation as well as savings associated with storing the antimicrobial compositions at warehouses, production facilities, and the like. Moreover, the antimicrobial compositions having enhanced solubility are generally provided in their solid state forms, thereby avoiding the problem of solutions freezing in colder climates during shipping.

The present disclosure can also reduce the health and safety risks associated with handling antimicrobial compositions that may contain hazardous substances. For example, opening a Menasha box or dropping water-soluble packaging into a container for dilution or reconstitution is much safer than opening any kind of container such as a drum, pail, or tote. Not only can the antimicrobial compositions having enhanced solubility be used to reduce health and safety risks, they can also aid in compliance with regulatory and safety requirements.

The present disclosure can also result in a smaller impact to the environment. For example, using water-soluble packaging as opposed to plastic containers for shipping will result in fewer plastic containers being thrown in the trash or recycled. In one realization of this disclosure, consumers can replenish household cleaning solutions by dropping a singleuse package of an antimicrobial composition into a plastic bottle (e.g. spray bottle) with water rather than purchasing a new ready-to-go cleaning solution from the store while discarding the old cleaning solution bottle.

The present disclosure can also simplify the manufacture of quaternary ammonium based antimicrobials. For example, the antimicrobial compositions having enhanced solubility eliminate the need for stirring solutions to dissolve quaternary ammonium salts, thereby eliminating not only physical apparatus from the production line (e.g. stirrers) but also the foaming and bubbles associated with the conventional solubilization methods.

Several exemplary formulations of antimicrobial compositions having enhanced solubility according to the present disclosure are provided below.

Formulation 1: 95 to 99% Solids Teat Dip (500 Gallon Mix)
Antimicrobial Composition:
  2.1 pounds CPC
  0.4 pounds monolaurin
  1.2 pounds Cola Lipid C
  1.0 pounds sodium bicarbonate or carrageenan
  20 to 50 ppm of EDTA Formulation 2: Hospital Disinfectant (1 Gallon Mix)
Antimicrobial Composition:
  300 grams TCM
  200 grams ADBAC
  15 grams sodium chloride
  20 to 50 ppm of EDTA Formulation 3: Hospital Disinfectant (1 Gallon Mix)
Antimicrobial Composition:
  300 grams TCM
  150 grams ADBAC
  50 grams CPC
  15 grams sodium chloride
  20 to 50 ppm of EDTA Formulation 4: Hospital Disinfectant (1 Gallon Mix)
Antimicrobial Composition:
  300 grams TCM
  150 grams ADBAC
  50 grams CPC
  15 grams sodium chloride
  0.01 to 8 grams methylisothiazolinone or chloromethylisothiazolinone
  20 to 50 ppm of EDTA Formulation 5: Truck Sanitizer (1 Gallon Mix)
Antimicrobial Composition:
  250 grams CTAC
  250 grams ADEBAC
  15 grams KATHON™ CG (methylchloroisothiazolinone/methylisothiazolinone)
  10 grams sodium bicarbonate
  20 to 50 ppm of EDTA Formulation 6: Truck Sanitizer (1 Gallon Mix)
Antimicrobial Composition:
  150 grams CTAC
  150 grams ADEBAC
  200 grams TCM, DCI, or TCI
  15 grams KATHON™ CG (methylchloroisothiazolinone/methylisothiazolinone)
  40 grams sodium bicarbonate
  20 to 50 ppm of EDTA Formulation 7: Poultry Processing (500 Gallon Mix)
Antimicrobial Composition:
  2.1 pounds CPC
  0.28 pounds urea
  0.44 pounds sodium bicarbonate
  20 to 50 ppm of EDTA Formulation 8: General Purpose Sanitizer (1 Gallon Mix)
Antimicrobial Composition:
  1.5 grams ADBAC
  1.5 grams ADEBAC
  3 grams sodium bicarbonate
  20 to 50 ppm of EDTA Formulation 9: Poultry Processing (1 Gallon Mix)
Antimicrobial Composition:
  1.9 grams CPC (500 ppm)
  1.9 grams sodium bicarbonate Formulation 10: Poultry Processing (1 Gallon Mix)
Antimicrobial Composition:
  2.3 grams CPC (600 ppm)
  2.3 grams sodium bicarbonate Formulation 11: Poultry Processing (1000 Gallon Mix)
Antimicrobial Composition:
  1.9 kilograms CPC (500 ppm)
  1.9 kilograms sodium bicarbonate Formulation 12: Poultry Processing (1000 Gallon Mix)
Antimicrobial Composition:
  2.3 kilograms CPC (600 ppm)
  2.3 kilograms sodium bicarbonate Formulation 13: Sanitizing (1 Gallon Mix or 1000 Gallon Mix)
Antimicrobial Composition (0.004165 lbs for 1 Gallon Mix; 4.165 lbs for 1000 Gallon Mix):
  BTAC—85.8% by weight
  urea—4% by weight
  sodium bicarbonate—10% by weight
  EDTA—0.2% by weight Formulation 14: Post-Harvest Wash (1 Gallon Mix or 1000 Gallon Mix)
Antimicrobial Composition (0.004165 lbs for 1 Gallon Mix; 4.165 lbs for 1000 Gallon Mix):
  CPC—92% by weight
  urea—2% by weight
  carrageenan—2% by weight
  sodium bicarbonate—4% by weight Formulation 15: Sanitizing (1 Gallon Mix or 1000 Gallon Mix)
Antimicrobial Composition (0.004165 lbs for 1 Gallon Mix; 4.165 lbs for 1000 Gallon Mix):
  BEC—48% by weight
  ADBAC—48% by weight
  Triton X-100—2% by weight
  carrageenan—2% by weight
  KATHON™ CG (methylchloroisothiazolinone/methylisothiazolinone)—15 ppm Those skilled in the art will appreciate that modifications are possible in the exemplary embodiments disclosed herein without materially departing from the novel teachings and advantages according to this disclosure. Accordingly, all such modifications and equivalents are intended to be included within the scope of this disclosure as defined in the following claims.

I claim:

1. An antimicrobial composition in unit dose form comprising:
    a water-soluble packaging encapsulating a powder formulation, the powder formulation comprising at least one antimicrobial quaternary ammonium compound and a water-soluble spacer compound interspersed therewith, wherein the quaternary ammonium compound is greater than 5% by weight of the antimicrobial composition.

2. The antimicrobial composition in unit dose form of claim 1, further comprising an oxidizer encapsulated by the water-soluble packaging, wherein the oxidizer is encapsulated separately from the at least one antimicrobial quaternary ammonium compound and the water-soluble spacer compound.

3. The antimicrobial composition in unit dose form of claim 1, further comprising a non-ionic surfactant encapsulated by the water-soluble packaging.

4. The antimicrobial composition in unit dose form of claim 1, further comprising an additional antimicrobial compound encapsulated by the water-soluble packaging.

5. The antimicrobial composition in unit dose form of claim 1, further comprising a chelator encapsulated by the water-soluble packaging.

6. The antimicrobial composition in unit dose form of claim 1, wherein the water-soluble packaging comprises polyvinyl alcohol or polyethylene oxide.

7. The antimicrobial composition in unit dose form of claim 1, wherein the at least one antimicrobial quaternary ammonium compound is selected from the group consisting of benzyltrimethylammonium chloride, benzethonium chloride, cetylpyridinium chloride, cetyltrimethylammonium chloride, alkyldimethylbenzylammonium chloride, alkyldimethylethylbenzylammonium chloride, didecyldimethylammonium chloride, dialkydimethylammonium chloride, cocamidopropyl PG-dimonium chloride phosphate, and combinations thereof.

8. The antimicrobial composition in unit dose form of claim 1, wherein the water-soluble spacer compound is selected from the group consisting of sodium bicarbonate, sodium chloride, urea, sugar, carrageenan, hydroxyethyl cellulose, methylcellulose, hydroxycellulose, and polyethylene oxide.

9. The antimicrobial composition in unit dose form of claim 2, wherein the oxidizer is selected from the group consisting of trichloromelamine, dichloroisocyanurate, trichloroisocyanurate, and potassium perborate.

10. The antimicrobial composition in unit dose form of claim 3, wherein the non-ionic surfactant is selected from the group consisting of an ethoxylated aliphatic alcohol, a polyoxyethylene surfactant, a carboxylic ester, a polyoxyethylene glycol ester, an anhydrosorbital ester, an ethoxylated derivative of an anhydrosorbital ester, a glycol ester of a fatty acids, a carboxylic amide, a monoalkanolamine condensate, and a polyoxyethylene fatty acid amide.

11. The antimicrobial composition in unit dose form of claim 3, further comprising a detergent selected from the group consisting of 4-(1,1,3,3-tetramethylbutyl)phenyl-polyethylene glycol, $C_{12-14}H_{25-29}O[CH_2CH_2O]_nH$, and sodium laurel sulfate.

12. The antimicrobial composition in unit dose form of claim 3, wherein the additional antimicrobial compound is selected from the group consisting of monolaurin, methylisothiazolinone, chloromethylisothiazolinone, nisin, and ε-polylysine.

13. The antimicrobial composition in unit dose form of claim 4, wherein the chelator is ethylenediaminetetraacetic acid.

14. The antimicrobial composition in unit dose form of claim 1, wherein the at least one antimicrobial quaternary ammonium compound is about 50% to about 95% by weight of the powder formulation and the water-soluble spacer compound is about 5% to about 50% by weight of the powder formulation.

15. The antimicrobial composition in unit dose form of claim 14, further comprising an oxidizer encapsulated by the water-soluble packaging, wherein the oxidizer is encapsulated separately from the at least one antimicrobial quaternary ammonium compound and the water-soluble spacer compound.

16. A method of making an antimicrobial composition in unit dose form comprising:
encapsulating a powder formulation comprising at least one antimicrobial quaternary ammonium compound and a water-soluble spacer compound interspersed therewith in a water-soluble packaging, wherein the quaternary ammonium compound is greater than 5% by weight of the antimicrobial composition.

17. The method of claim 16, further comprising encapsulating an oxidizer in the water-soluble packaging, wherein the oxidizer is encapsulated separately from the at least one antimicrobial quaternary ammonium compound and the water-soluble spacer compound.

18. A method for sanitizing using an antimicrobial composition comprising:
dissolving the antimicrobial composition according to claim 1 in a solvent to form a cleaning solution; and
contacting an area or an item with the cleaning solution.

19. The method of claim 18, wherein the solvent is water.

* * * * *